US010889601B2

(12) United States Patent
MacGillivray et al.

(10) Patent No.: US 10,889,601 B2
(45) Date of Patent: Jan. 12, 2021

(54) SEPARATIONS USING BORON CONTAINING HYDROCARBON SPONGES

(71) Applicant: UNIVERSITY OF IOWA RESEARCH FOUNDATION, Iowa City, IA (US)

(72) Inventors: Leonard MacGillivray, Iowa City, IA (US); Gonzalo Campillo-Alvarado, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 16/788,027

(22) Filed: Feb. 11, 2020

(65) Prior Publication Data
US 2020/0255454 A1 Aug. 13, 2020

Related U.S. Application Data

(60) Provisional application No. 62/804,052, filed on Feb. 11, 2019.

(51) Int. Cl.
*C07F 5/02* (2006.01)
*C07C 7/12* (2006.01)
*C07D 333/10* (2006.01)

(52) U.S. Cl.
CPC .............. *C07F 5/025* (2013.01); *C07C 7/12* (2013.01); *C07D 333/10* (2013.01)

(58) Field of Classification Search
CPC ........................................................ C07F 5/02
USPC ........................................................ 546/13
See application file for complete search history.

(56) References Cited

U.S. PATENT DOCUMENTS

| | | | |
|---|---|---|---|
| 4,559,157 | A | 12/1985 | Smith et al. |
| 4,608,392 | A | 8/1986 | Jacquet et al. |
| 4,820,508 | A | 4/1989 | Wortzman |
| 4,992,478 | A | 2/1991 | Geria |
| 9,669,115 | B2 | 6/2017 | MacGillivray |
| 9,937,177 | B2 | 4/2018 | MacGillivray |
| 2011/0223203 | A1 | 9/2011 | Berkland et al. |
| 2012/0128740 | A1 | 5/2012 | Filipcsei et al. |

OTHER PUBLICATIONS

Barba, V., et al., "Boron-nitrogen macrocycles: a new generation of calix[3]arenes", Chem Commun 2834-2835 (2004).
Benedict, "Stereotactic body radiation therapy: The report of AAPM Task Group 101", Med. Phys. 37 (8), 4078-4101 (2010).
Bucar, et al., "Preparation and Reactivity of Nanocrystalline Cocrystals Formed via Sonocrystallization", Journal of the American Chemical Society, 129, 32-33 (2007).
Campillo-Alvarado, G , et al., "Exploiting Boron Coordination: N → B Bond Supports a [2+2] Photodimerization in the Solid State and Generation of a Diboron Bis-Tweezer for Benzene/Thiophene Separation", Angewandte Chemie 58(16), 5413-5416 (2019).
Campillo-Alvarado, G, et al., "Self-Assembly of Fluorinated Boronic Esters and 4,4'-Bipyridine into 2:1 N→B Adducts and Inclusion of Aromatic Guest Molecules in the Solid State: Application for the Separation of o,m,p-Xylene", Cryst Growth Des 18(5), 2726-2743 (2018).
Caronna, T, et al., "Halogen Bonding and π—π Stacking Control Reactivity in the Solid State", J. Am Chem Soc 126(14), 4500-4501 (2004).
De Vries, et al., "Block-Copolymer-Stabilized Iodinated Emulsions for Use as CT Contrast Agents", Biomater. 31, 6537-6544 (2010).
Dekrafft, "Iodinated Nanoscale Coordination Polymers as Potential Contrast Agents for Computed Tomography", Angew. Chem. Int. Ed. Engl., 48, 9901-9904 (2009).
Dudovitz, et al., "Polymorphic Hydrogen-bonding Motifs and Reactivity in Co-crystals of 5-fluorouracil", Presented at the 11th Annual Spring Undergraduate Research Festival, University of Iowa, #30, 2 pages, Apr. 8, 2015.
Duncan, A, et al., "Quantitative and regiocontrolled corss-photocycloaddition of the anticancer drug 5-fluorouracil achieved in a cocrystal", Chem Commun 52, 13109-13111 (2016).
Gao, X, et al., "Supramolecular Construction of Molecular Ladders in the Solid State", Angewandte Chemie 43(2), 232-236 (2003).
Hahn, et al., "Nanoparticles as Contrast Agents for in-vivo Bioimaging: Current Status and Future Perspectives", Anal Bioanal. Chem., 399, 3-27 (2011).
Herrera-Espana, A, et al., "Selective Isolation of Polycyclic Aromatic Hydrocarbons by Self-Assembly of a Tunable N→B Clathrate", Crystal Growth & Design 15(4), 1572-1576 (2015).
Jin, Q, et al., "Biocompatible Drug Delivery System for Photo-Triggered Controlled Release of 5-Fluorouracil", Biomacromolecules 12(10), 3684-3691 (2011).
Kong, et al., "Nanoparticulate carrier containing water-insoluble iodinated oil as a multifunctional contrast agent for computed tomography imaging", Biomater. 28, 5555-5561 (2007).

(Continued)

*Primary Examiner* — Charanjit Aulakh
(74) *Attorney, Agent, or Firm* — Viksnins Harris Padys Malen LLP

(57) ABSTRACT

The invention provides a compound of formula (I):

(I)

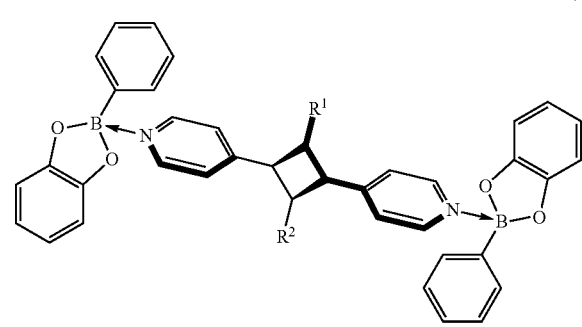

or a salt thereof, wherein $R^1$ and $R^2$ have any of the values defined in the specification, as well as methods of using such compounds and salts to separate an aryl compound from a mixture.

20 Claims, 8 Drawing Sheets
(8 of 8 Drawing Sheet(s) Filed in Color)

(56) References Cited

OTHER PUBLICATIONS

Li, S, et al., "Charge-Transfer Emitting Triarylborane π-Electron Systems", Inorg Chem 56, 8705-8717 (2017).

Liu, Z, et al., "B—N versus C—C: How Similar Are They?", Angew Chem Int Ed 47, 242-244 (2008).

Martin, "Synthesis and N.M.R. Spectra of Substituted Aminoiodoacridines", Aust. J. Chem., 32(12), 2637-2646 (1979).

McIntire, et al., "Pulmonary Delivery of Nanoparticles of Insoluble, Iodinated CT X-ray Contrast Agents to Lung Draining Lymph Nodes in Dogs", J. Pharm. Sci. 87, 1466-1470 (1998).

McWhinnie, et al., "Mono- and Bimetallic Bipyridyl Polyene Complexes Containing 17-Electron Molybdenum Mononitrosyl Centers: Electrochemical, Spectroscopic, and Magnetic Studies", Inrg. Chem. 35(3), 760-774 (1996).

Oburn, S, et al., "Supramolecular Construction of an Aldehyde-Cyclobutane via the Solid State: Combining Reversible Imine Formation and Metal-Organic Self-Assembly", J Am Chem Soc 139, 8452-8454 (2017).

Sander, "Expansions of supramolecular chemistry: nanocrystals, pharmaceutical cocrystals, imaging, and decorated olefins", Ph.D. dissertation, University of Iowa, 223 pages 2012.

Sander, et al., "Pharmaceutical Nono-Cocrystals: Sonochemical Synthesis by Solvent Selection and Use of a Surfactant", Angew. Chem. Int. Ed. 49, 7284-7288 (2010).

Sekhon, B, "Pharmaceutical co-crystals—a review", ARS Pharmaceutica 50(3), 99-117 (2009).

Sinnwell, M, et al., "Combination of Argentophilic and Perfluorophenyl-Perfluorophenyl Interactions Supports a Head-to-Head [2+2] Photodimerization in the Solid State", Cryst Growth Des 15, 538-541 (2015).

Sinnwell, M, et al., "Halogen-Bond-Templated [2+2] Photodimerization in the Solid State: Directed Synthesis and Rare Self-Inclusion of a Halogenated Product", Angew Chem Int Ed Engl 55(10), 3477-3480 (2016).

Whitesides, et al., "Molecular Self-Assembly and Nanochemistry: A Chemical Strategy for the Synthesis of Nanostructures", Science 254, 1312-1319 (1991).

Wikipedia, "Diatrizoic acid", (2015).

Yan, D, et al., "A Cocrystal Strategy to Tune the Luminescent Properties of Stilbene-Type Organic Solid-State Materials", Angewandte Chemie 123(52), 12691-12694 (2011).

SEPARATIONS USING BORON CONTAINING HYDROCARBON SPONGES

RELATED APPLICATION

This application claims priority to U.S. Provisional Patent Application No. 62/804,052 that was filed on Feb. 11, 2019. The entire content of the application referenced above is hereby incorporated by reference herein.

STATEMENT REGARDING FEDERALLY SPONSORED RESEARCH

This invention was made with government support under 1708673 awarded by the National Science Foundation. The government has certain rights in the invention.

BACKGROUND

The use of noncovalent bonds to support the organization of alkenes in solids to undergo [2+2]-photocycloadditions has received considerable attention. Hydrogen bonds (L. R. MacGillivray, et al., *J. Am. Chem. Soc.* 2004, 126, 4500-4501), halogen bonds (M. A. Sinnwell, L. R. MacGillivray, *Angew. Chem. Int. Ed.* 2016; and T. Caronna, et al., *J. Am. Chem. Soc.* 2004, 126, 4500-4501), and coordination bonds involving transition-metal-ions (Q. Chu, et al., *Cryst. Growth Des.* 2015, 15, 538-541; M. A. Sinnwell, et al., *Cryst. Growth Des.* 2015, 15, 538-541; and S. M. Oburn, et al., *J. Am. Chem. Soc.* 2017, 139, 8452-8454) have been exploited to direct the photoreaction. The noncovalent—or supramolecular—strategy to direct reactivity in the solid state has developed to allow chemists to use the covalent-bond-forming reaction to modify bulk physical properties of solids (e.g. optical, see D. Yan, et al., *Angew. Chem.* 2011, 123, 12691-12694) and synthesize novel molecules (e.g. ladderanes, see X. Gao, et al., *Angew. Chem. Int. Ed.* 2004, 43, 232-236)) with virtually perfect control of stereochemistry.

In recent years, coordination to boron has been used to generate supramolecular host materials (A. D. Herrera-España, et al., *Cryst. Growth Des.* 2015, 15, 1572-1576; and G. Campillo-Alvarado, et al., *Cryst. Growth Des.* 2018, 18, 2726-2743). Upon interacting with a pyridyl moiety, the B-atom of an aromatic boronic ester, for example, will undergo a planar-to-tetrahedral change in geometry such that the pyridyl group adopts an orthogonal orientation with respect to the ester (FIG. 1). The twisted geometry will generate an electron-deficient cavity that can host a variety of electron-rich molecules (e.g. aromatics) as guests (FIG. 1a). The 'heterogeneous/ionic' character of the N→B bond (Z. Liu, T. B. Marder, *Angew. Chem. Int. Ed.* 2008, 47, 242-244) is attractive to generate materials with unique electronic (S.-Y. Li, et al., *Inorg. Chem.* 2017, 56, 8705-8717) and/or inclusion (V. Barba, et al., *Chem. Commun.* 2004, 2834-2835) properties.

SUMMARY

In one embodiment, the invention provides a compound of formula (I):

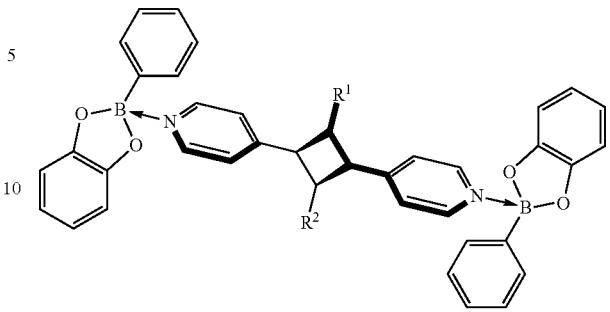

(I)

or a salt thereof, wherein:

$R^1$ is aryl or heteroaryl that is optionally substituted with one or more groups independently selected from the group consisting of nitro, carboxy, halo, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, OH and $C(=O)(C_1-C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, —OH and cyano; and $R^2$ is aryl or heteroaryl that is optionally substituted with one or more groups independently selected from the group consisting of nitro, carboxy, halo, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, OH and $C(=O)(C_1-C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, OH and cyano.

In another embodiment, the invention provides a method for separating an aryl compound from a mixture comprising the aryl compound, said method comprising contacting the mixture with a ditopic boronic ester adduct, under conditions such that the aryl compound is separated from the mixture.

In another embodiment, the invention provides a method for purifying a hydrocarbon that comprises an impurity, comprising contacting a mixture comprising the hydrocarbon and the impurity with a ditopic boronic ester adduct under conditions such that the hydrocarbon is separated from the impurity.

BRIEF DESCRIPTION OF THE FIGURES

The patent or application file contains at least one drawing executed in color. Copies of this patent or patent application publication with color drawings will be provided by the Office upon request and payment of the necessary fee.

DETAILED DESCRIPTION

Figure 1:
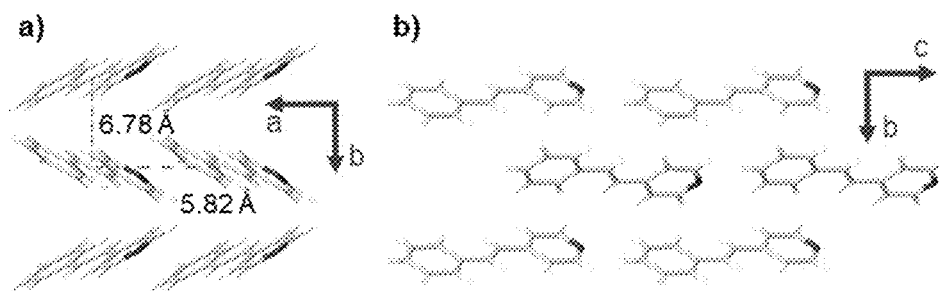
FIG. 1. X-ray structure 4-sbz: (a) herringbone motif in ab-plane and (b) extended packing in bc-plane FIG. 2. X-ray structure (1)·(4-sbz): (a) ORTEP view of face-to-face π-stacks and (b) extended view along bc-plane FIG. 3. X-ray structure bis-tweezer 2(1)·(ht-ppcb)⊃2 ($C_6H_6$): (a) ORTEP view of diboron adduct, (b) packing of adducts, and (c) benzene inclusion.

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples include ($C_1$-$C_8$)alkyl, ($C_2$-$C_8$)alkyl, $C_1$-$C_6$)alkyl, ($C_2$-$C_6$)alkyl and ($C_3$-$C_6$)alkyl. Examples of alkyl groups include methyl, ethyl, n-propyl, iso-propyl, n-butyl, t-butyl, iso-butyl, sec-butyl, n-pentyl, n-hexyl, n-heptyl, n-octyl, and and higher homologs and isomers.

The term "alkenyl" refers to an unsaturated alkyl radical having one or more double bonds. Examples of such unsaturated alkyl groups include vinyl, 2-propenyl, crotyl, 2-isopentenyl, 2-(butadienyl), 2,4-pentadienyl, 3-(1,4-pentadienyl) and the higher homologs and isomers.

The term "alkynyl" refers to an unsaturated alkyl radical having one or more triple bonds. Examples of such unsaturated alkyl groups ethynyl, 1- and 3-propynyl, 3-butynyl, and higher homologs and isomers.

The term "alkoxy" refers to an alkyl groups attached to the remainder of the molecule via an oxygen atom ("oxy").

The term "alkylthio" refers to an alkyl groups attached to the remainder of the molecule via a thio group.

The term "cycloalkyl" refers to a saturated or partially unsaturated (non-aromatic) all carbon ring having 3 to 8 carbon atoms (i.e., ($C_3$-$C_8$)carbocycle). The term also includes multiple condensed, saturated all carbon ring systems (e.g., ring systems comprising 2, 3 or 4 carbocyclic rings). Accordingly, carbocycle includes multicyclic carbocyles such as a bicyclic carbocycles (e.g., bicyclic carbocycles having about 3 to 15 carbon atoms, about 6 to 15 carbon atoms, or 6 to 12 carbon atoms such as bicyclo[3.1.0] hexane and bicyclo[2.1.1]hexane), and polycyclic carbocycles (e.g tricyclic and tetracyclic carbocycles with up to about 20 carbon atoms). The rings of the multiple condensed ring system can be connected to each other via fused, spiro and bridged bonds when allowed by valency requirements. For example, multicyclic carbocyles can be connected to each other via a single carbon atom to form a spiro connection (e.g., spiropentane, spiro[4,5]decane, etc), via two adjacent carbon atoms to form a fused connection (e.g., carbocycles such as decahydronaphthalene, norsabinane, norcarane) or via two non-adjacent carbon atoms to form a bridged connection (e.g., norbornane, bicyclo[2.2.2]octane, etc). Non-limiting examples of cycloalkyls include cyclopropyl, cyclobutyl, cyclopentyl, cyclohexyl, bicyclo[2.2.1] heptane, pinane, and adamantane.

The term "aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed carbon ring systems (e.g., ring systems comprising 2, 3 or 4 rings) having about 9 to 20 carbon atoms in which at least one ring is aromatic and wherein the other rings may be aromatic or not aromatic (i.e., cycloalkyl. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Non-limiting examples of aryl groups include, but are not limited to, phenyl, indenyl, indanyl, naphthyl, 1, 2, 3, 4-tetrahydronaphthyl, anthracenyl, and the like.

The term "heterocycle" refers to a single saturated or partially unsaturated ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems are further described below. Thus, the term includes single saturated or partially unsaturated rings (e.g., 3, 4, 5, 6 or 7-membered rings) from about 1 to 6 carbon atoms and from about 1 to 3 heteroatoms selected from the group consisting of oxygen, nitrogen and sulfur in the ring. The sulfur and nitrogen atoms may also be present in their oxidized forms. Exemplary heterocycles include but are not limited to azetidinyl, tetrahydrofuranyl and piperidinyl. The term "heterocycle" also includes multiple condensed ring systems (e.g., ring systems comprising 2, 3 or 4 rings) wherein a single heterocycle ring (as defined above) can be condensed with one or more groups selected from cycloalkyl, aryl, and heterocycle to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system including a heterocycle, aryl and carbocycle portion of the ring. In one embodiment the term heterocycle includes a 3-15 membered heterocycle. In one embodiment the term heterocycle includes a 3-10 membered heterocycle. In one embodiment the term heterocycle includes a 3-8 membered heterocycle. In one embodiment the term heterocycle includes a 3-7 membered heterocycle. In one embodiment the term heterocycle includes a 3-6 membered heterocycle. In one embodiment the term heterocycle includes a 4-6 membered heterocycle. In one embodiment the term heterocycle includes a 3-10 membered monocyclic or bicyclic heterocycle comprising 1 to 4 heteroatoms. In one embodiment the term heterocycle includes a 3-8 membered monocyclic or bicyclic heterocycle heterocycle comprising 1 to 3 heteroatoms. In one embodiment the term heterocycle includes a 3-6 membered monocyclic heterocycle comprising 1 to 2 heteroatoms. In one embodiment the term heterocycle includes a 4-6 membered monocyclic heterocycle comprising 1 to 2 heteroatoms. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one imidazolidine, pyrazolidine, butyrolactam, valerolactam, imidazolidinone, hydantoin, dioxolane, phthalimide, and 1,4-dioxane.

The term "heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. In one embodiment, the heteroaryl is a 5-20 membered heteroaryl. In another embodiment, the heteroaryl is a 5-10 membered heteroaryl. In another embodiment, the heteroaryl is a 5-membered aryl. In another embodiment, the heteroaryl is a 6-membered heteroaryl. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from cycloalkyl, aryl, heterocycle, and heteroaryl. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, triazolyl, tetrazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, and quinazolyl.

The term "alkoxycarbonyl" as used herein refers to a group (alkyl)-O'C(=O)—, wherein the term alkyl has the meaning defined herein.

The term "alkanoyloxy" as used herein refers to a group (alkyl)-C(=O)—O—, wherein the term alkyl has the meaning defined herein.

As used herein, the term "heteroatom" is meant to include oxygen (O), nitrogen (N), sulfur (S) and silicon (Si).

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein a wavy line "〰" that intersects a bond in a chemical structure indicates the point of attachment of the bond that the wavy bond intersects in the chemical structure to the remainder of a molecule.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process.

The terms "racemic mixture" and "racemate" refer to an equimolar mixture of two enantiomeric species, devoid of optical activity.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

Specific values listed below for radicals, substituents, and ranges, are for illustration only; they do not exclude other defined values or other values within defined ranges for the radicals and substituents. It is to be understood that two or more values may be combined. It is also to be understood that the values listed herein below (or subsets thereof) can be excluded.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$ eyeloalkyl can be cyclopropyl, cyclobutyl, cyclopentyl, or cyclohexyl; $(C_3-C_6)$ eyeloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$ alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ is phenyl optionally substituted with one or more groups independently selected from the group consisting of nitro, halo, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, —OH and —C(=O)$(C_1-C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, —OH and cyano.

A specific value for $R^1$ is 2,3,4,5,6-fluorophenyl.

A specific value for $R^1$ is phenyl.

A specific value for $R^1$ is thiophenyl optionally substituted with one or more groups independently selected from the group consisting of nitro, halo, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, —OH and —C(=O)$(C_1-C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, —OH and cyano.

A specific value for $R^1$ is thiophenyl.

A specific value for $R^2$ is phenyl optionally substituted with one or more groups independently selected from the group consisting of nitro, halo, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, —OH and —C(=O)$(C_1-C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, —OH and cyano.

A specific value for $R^2$ is 2,3,4,5,6-fluorophenyl.

A specific value for $R^2$ is phenyl.

A specific value for $R^2$ is thiophenyl optionally substituted with one or more groups independently selected from the group consisting of nitro, halo, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, —OH and —C(=O)$(C_1-C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, OH and cyano.

A specific value for $R^2$ is thiophenyl.

In one embodiment, the aryl compound is benzene, fluorobenzene, chlorobenzene, bromobenzene, iodobenzene, hydroxybenzene, aniline, furan, thiophene, 2-methylthiophene, 3-methylthiophene, 2,4-dimethylthiophene, benzothiophene, 2,3-dimethylbenzothiophene, 2,3,7-trimethylbenzothiophene, 2,3,4,7-tetramethylbenzothiophene, 2-methylbenzothiophene, dibenzothiophene, 4,6-dimethyldibenzothiophene, 2,4,6-dimethyldibenzothiophene, toluene, o-xylene, m-xylene, p-xylene, mesitylene, naphthalene, anthracene, phenanthrene, pyrene, coronene, tetrathiafulvalene, styrene or stilbene.

In one embodiment, the mixture comprising the aryl compound further comprises a non-aromatic organic solvent.

In one embodiment, the non-aromatic organic solvent is selected from the group consisting of halocarbons, ketones, esters, tetrahydrofuran, acetonitrile, dimethylformamide, and dialkyl ethers.

In one embodiment, the non-aromatic organic solvent is selected from the group consisting of chloroform, dichloromethane, carbon tetrachloride, acetone, ethyl acetate, tetrahydrofuran, acetonitrile, dimethylformamide, and diethylether.

In one embodiment, the ditopic boronic ester adduct is selected from the group consisting of:

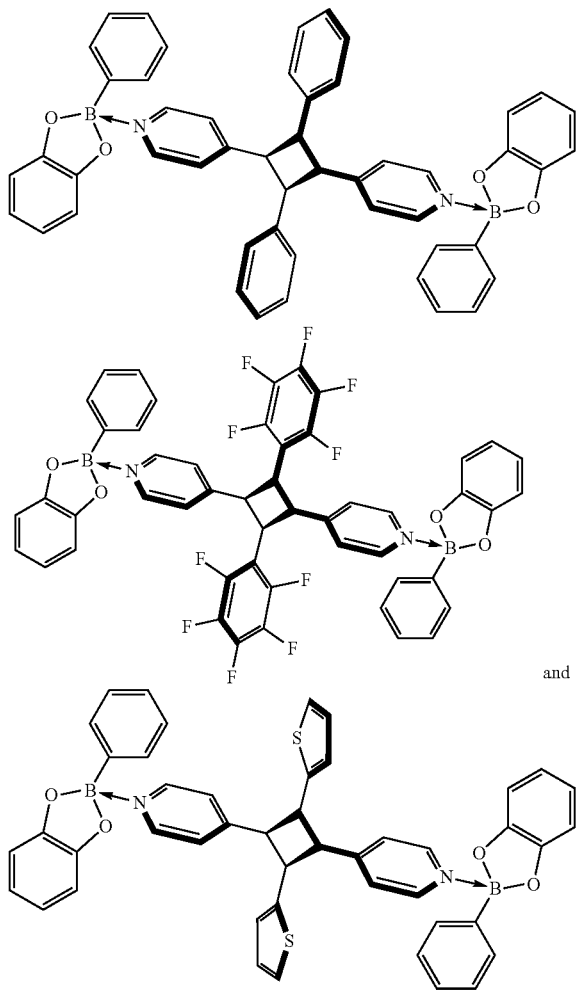

or is a salt thereof.

In one embodiment, the impurity is benzene, thiophene, toluene, o-xylene or stilbene.

In one embodiment, the invention provides the compound 2(1)-(ht-ppcb):

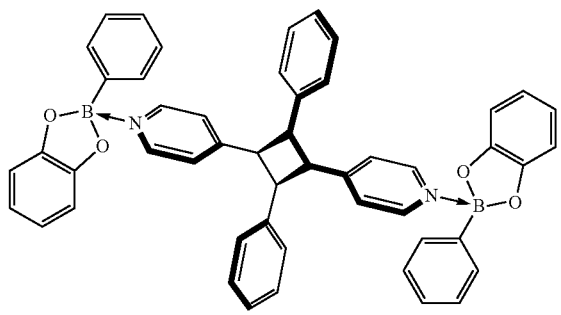

In another embodiment, the invention provides a method for separating benzene and thiophene comprising contacting a mixture comprising benzene and thiophene with a ditopic boronic ester adduct (e.g., 2(1)-(ht-ppcb)).

In another embodiment, the invention provides a method for separating thiophene and benzene, comprising contacting a mixture comprising thiophene and benzene with a ditopic boronic ester adduct, under conditions such that the thiophene is separated from the benzene.

In another embodiment, the invention provides a method for separating a first hydrocarbon from a second hydrocarbon comprising contacting a mixture comprising the first hydrocarbon and the second hydrocarbon with a ditopic boronic ester adduct (e.g., 2(1)-(ht-ppcb)) under conditions such that the first hydrocarbon is separated from the second hydrocarbon.

In another embodiment, the invention provides a method for separating a thiophene and a second hydrocarbon comprising contacting a mixture comprising thiophene and the second hydrocarbon with a ditopic boronic ester adduct (e.g., 2(1)-(ht-ppcb)) under conditions such that the thiophene is separated from the second hydrocarbon.

In another embodiment, the invention provides a method for purifying a hydrocarbon that comprises an impurity comprising contacting a mixture comprising the hydrocarbon and the impurity with a ditopic boronic ester adduct (e.g., 2(1)-(ht-ppcb)) under conditions such that the hydrocarbon is separated from the impurity.

In cases where compounds are sufficiently basic or acidic, a salt of a compound of formula I can be useful as an intermediate for isolating or purifying a compound of formula I. Salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The invention reports the first use of the N→B bond to support a [2+2] photodimerization in the solid state. This work demonstrates the orthogonal geometry adopted by coordination of the unsymmetrical monopyridine 4-sbz to the catechol ester of phenylboronic acid (1) in H(1)·(4-sbz) to enable dimeric face-to-face and head-to-tail (ht) π-stacking of the alkene with the carbon-carbon double (C=C) bonds being in the geometry of Schmidt (G. Schmidt, *Pure Appl. Chem.* 1971, 27, 647-678) for a photodimerization. Calculations performed using the Hartree-Fock method (HF/3-21G basis set) reveal the ht-orientation of the coordinated alkenes to be influenced by complementary stacking between electron-deficient (pyridyl) and electron-rich (phenyl) rings. Exposure of (1) (4-sbz) to UV-radiation generates ht-rctt-1,3-bis(4'-pyridyl)-2,4 bis(phenyl)cyclobutane (ht-ppcb) as 2(1)·(ht-ppcb) regioselectively and in quantitative yield. This work demonstrates the application of ht-ppcb to form a novel bis-tweezer host in 2(1)·(ht-ppcb) that enables the separation industrially relevant benzene/thiophene mixtures.

As a pure solid, 4-sbz is photostable (see ESI). The alkene self-assembles in a herringbone motif with nearest-neighbor carbon-carbon double (C=C) bonds separated by 5.82 Å (FIG. 1) (CSD codename: EDUREA) (E. Cariati, et al., *New J. Chem.* 2002, 26, 13-15).

The C=C bond of 4-sbz is made photoactive when 4-sbz engages in N→B coordination with 1. Slow evaporation of a solution of 4-sbz (7.4 mg, 0.041 mmol) and 1 (8.0 mg, 0.041 mmol) in benzene (3 mL) yielded single crystals as colorless plates of (1)·(4-sbz) after a period of ca 2 d. The formulation of (1)·(4-sbz) was confirmed using $^1$H NMR spectroscopy, as well as single-crystal and powder X-ray diffraction.

Figure 2:
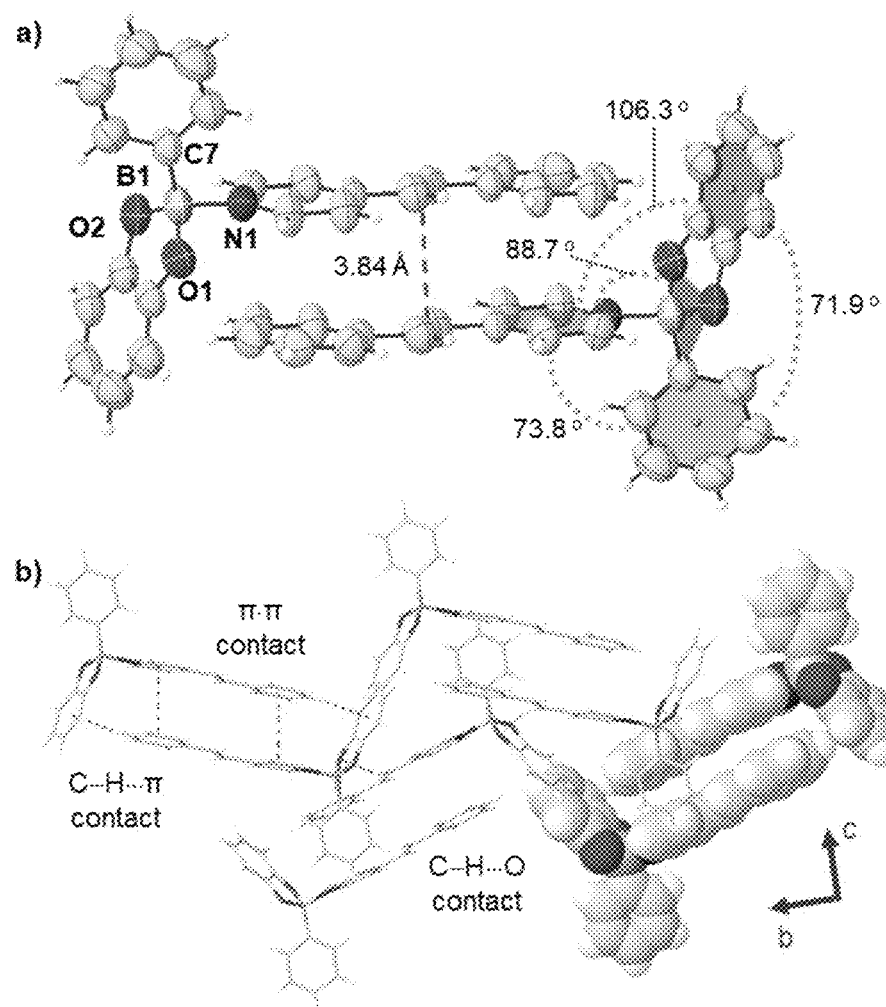

The components of (1)·(4-sbz) crystallize in the monoclinic space group P 2$_1$/n (FIG. 2). The ester 1 and 4-sbz interact via a N→B bond (1.632(4) Å). The bond is slightly stronger than comparative bonds with boronic esters, as exemplified by the tetrahedral character (THC=77.7%) (FIG. 2a) (H. Höpfl, *J. Organomet. Chem.* 1999, 581, 129-149). The alkene adopts a nearly-planar conformation (dihedral angle: 4.4°) and lies approximately orthogonal (88.7°) to the plane of donor atoms C7, O1, and O2. As a consequence of the assembly process, the N→B coordination affords a monoboron adduct that adopts an overall T-shaped geometry. The adduct assembles as a discrete dimers, which sits around a crystallographic center of inversion, with the coordinated alkenes participating in face-to-face π-π forces. The face-to-face stacking is attributed to complementary electrostatic interactions. Hartree-Fock calculations reveal the coordinated pyridyl and phenyl groups of (1)·(4-sbz) to be highly-electron deficient and rich, respectively (see Supporting Information). The stacked alkenes, thus, adopt a ht-orientation with the C=C bonds being parallel and separated by 3.84 Å (FIG. 2a). The geometry conforms to the postulate of Schmidt (G. Schmidt, *Pure Appl. Chem.* 1971, 27, 647-678). Adjacent adducts interact via side-on C—H . . . π forces (C . . . π(cent) 3.566(4) Å). The interactions afford layers (dihedral: 31.6°) within the crystallographic bc-plane (FIG. 2b). C=C bonds of neighboring adducts are separated >9.0 Å.

The N→B monoadduct (1)·(4-sbz) is highly photoreactive. When a crystalline powder of (1)·(4-sbz) was exposed to broadband UV radiation (medium-pressure Hg lamp) for only 20 min, a $^1$H NMR spectroscopic analysis revealed the alkene to react regioselectively and in quantitative yield. The photoreaction was evidenced by the disappearance of the olefinic signals and appearance of a signal in the cyclobutane region (4.51 ppm).

To confirm the stereochemistry of the photoproduct, a sample (15 mg, 0.020 mmol) of the reacted solid was dissolved in benzene/chloroform (3 mL, ratio: 1:1). Single crystals of 2(1)·(ht-ppcb)⊃2(C$_6$H$_6$) as yellow prisms formed upon slow evaporation after a period of 1 d. The composition of 2(1)·(ht-ppcb)⊃2(C$_6$H$_6$) was confirmed using $^1$H NMR spectroscopy and single-crystal X-ray diffraction.

Figure 3:
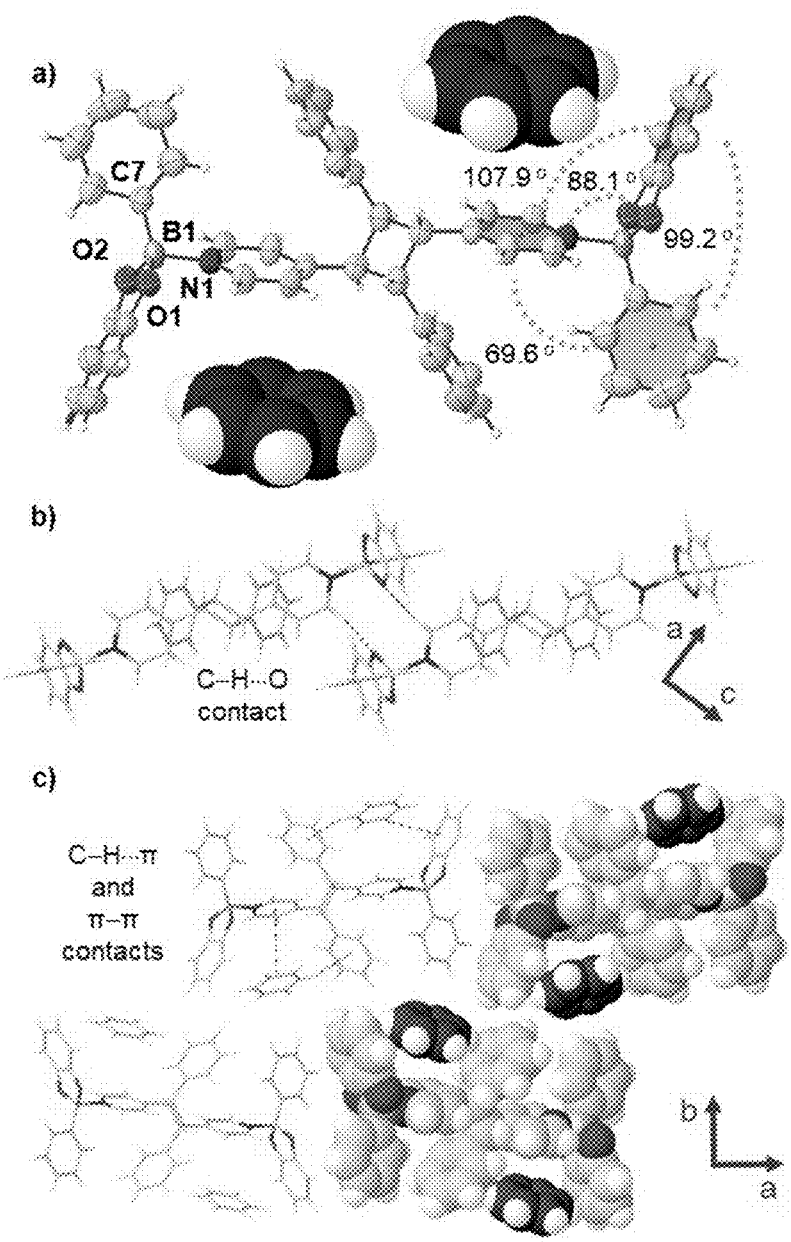
Figure 4:
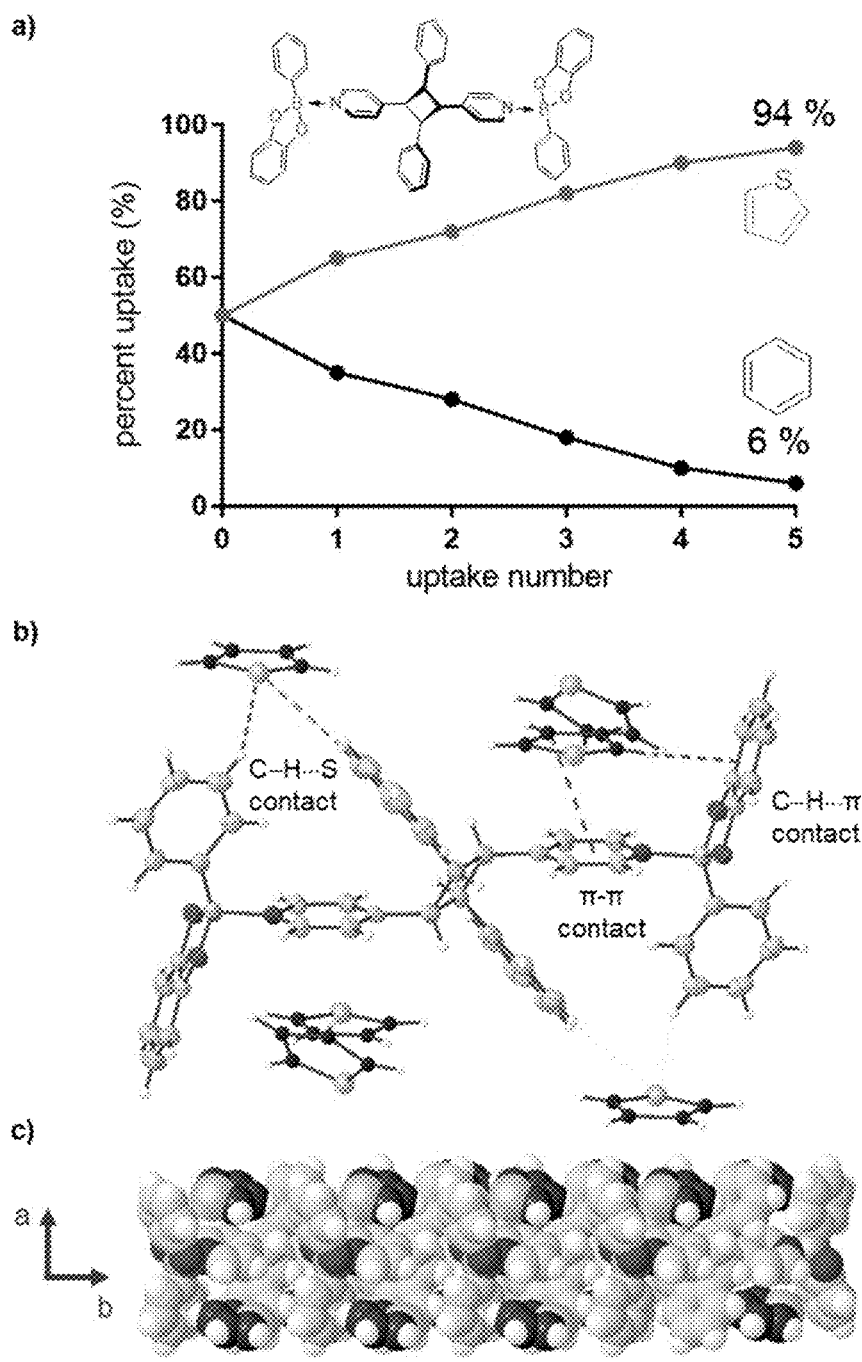
FIG. 4. Thiophene uptake: (a) relative percent vs. uptake number, (b) ORTEP view of X-ray structure 2(1)·(ht-ppcb)⊃6(C$_4$H$_4$S) highlighting thiophene contacts, and (c) extended view along ab-plane.

The components of 2(1)·(ht-ppcb)⊃2(C$_6$H$_6$) crystallize in the monoclinic space group P 2$_1$/n (FIG. 3). The X-ray structure determination confirms the stereochemistry of ht-ppcb (corner angles: 104.8°, 47.8°). The components form a three-component diboron assembly, which sits around a crystallographic center of inversion, that entraps benzene as a guest (FIG. 3a). The N→B bond (1.639(4) Å) is slightly weaker than unreacted (1)·(4-sbz) (THC 75.4%) (H. Höpfl, *J. Organomet. Chem.* 1999, 581, 129-149), while the orthogonality of the pyridyls to the plane of C7, O2, O3 is retained (88.1°) (FIG. 3b). Importantly, the orientations of the terminal phenyl rings give rise to two identical cavities defined by the obtuse corner angles of the cyclobutane ring. Each cavity hosts a single benzene molecule. Collectively, the structural metrics make the diboron adduct 2(1)·(ht-ppcb) a rare example (J. S. Park, J. L. Sessler, *Acc. Chem. Res.* 2018, ASAP; G. Li, et al., *Sens Actuators B Chem.* 2018, 259, 177-182; G. Li, et al., *Anal. Chem.* 2016, 88, 10751-10756; K. A. Nielsen, et al., *J. Am. Chem. Soc.* 2004, 126, 16296-16297; and M. Hardouin-Lerouge, et al., *Chem. Soc. Rev.* 2011, 40, 30-43) of a bis-tweezer host (FIG. 3c). Previous bis-tweezers exploit the 1,3'-alternate conformation of calix[4]arenes and pyrroles to form electron-rich double cavities that entrap electron-poor guests. Here, the pyridyl and phenyl rings form cavities suitable to accommodate an electron rich guest that interacts via a combination of face-to-face (pyridine) and edge-to-face (phenyl) π-forces.

Figure 5:
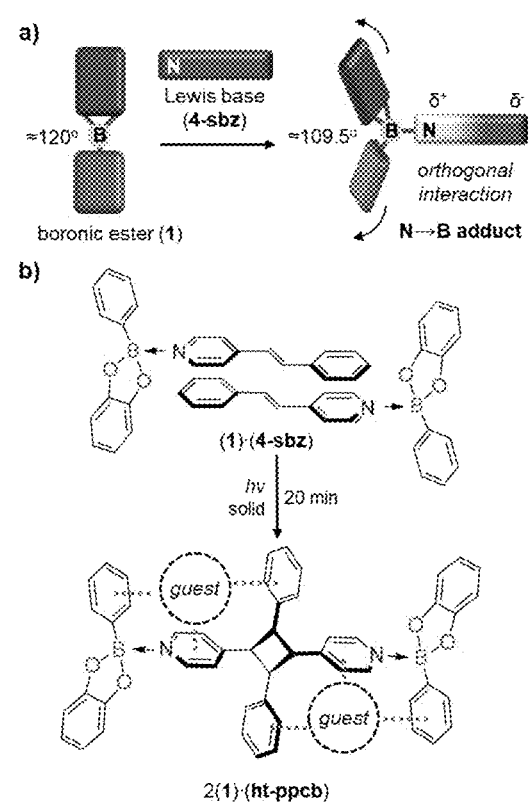
FIG. 5. (a) Orthogonal interaction of boronic ester 1 with a Lewis base and (b) head-to-tail [2+2] photodimerization of 4-sbz supported by 1 and generation of diboron tweezer 2(1)·(ht-ppcb).
Figure 6:
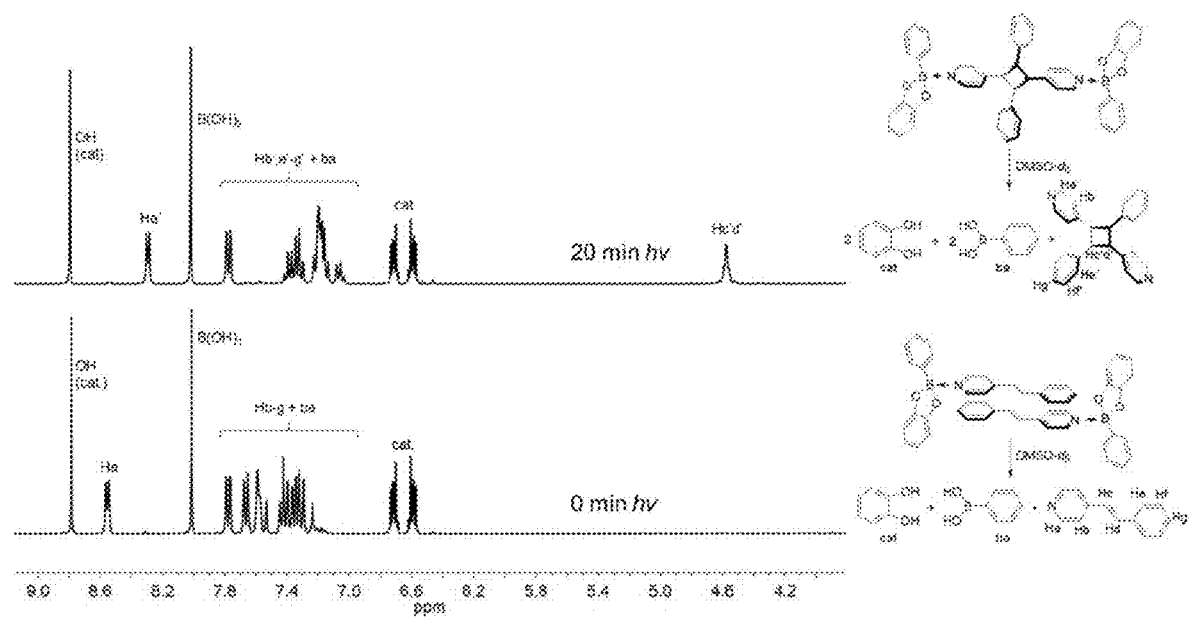
FIG. 6. $^1$H NMR spectra of (1)·(4-sbz) before (bottom) and after 20 min UV irradiation to afford 2(1)·(ht-ppcb) (top) (300 MHz, DMSO-d$_6$).
Figure 7:
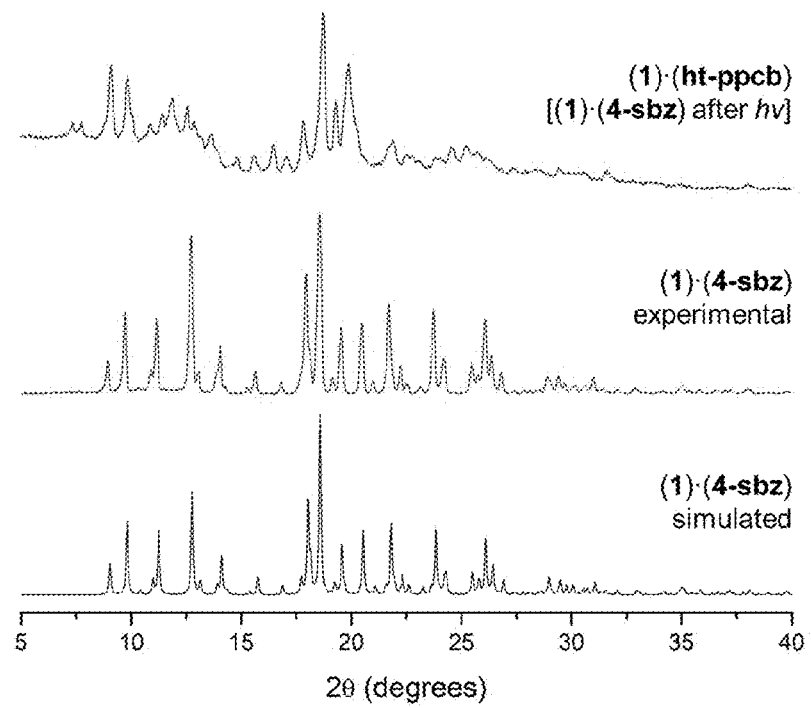
FIG. 7. PXRD patterns of (1)·(4-sbz) simulated from crystal structure, (1)·(4-sbz) experimental before and after UV irradiation for 20 min [2(1)·(ht-ppcb)].
Figure 8:
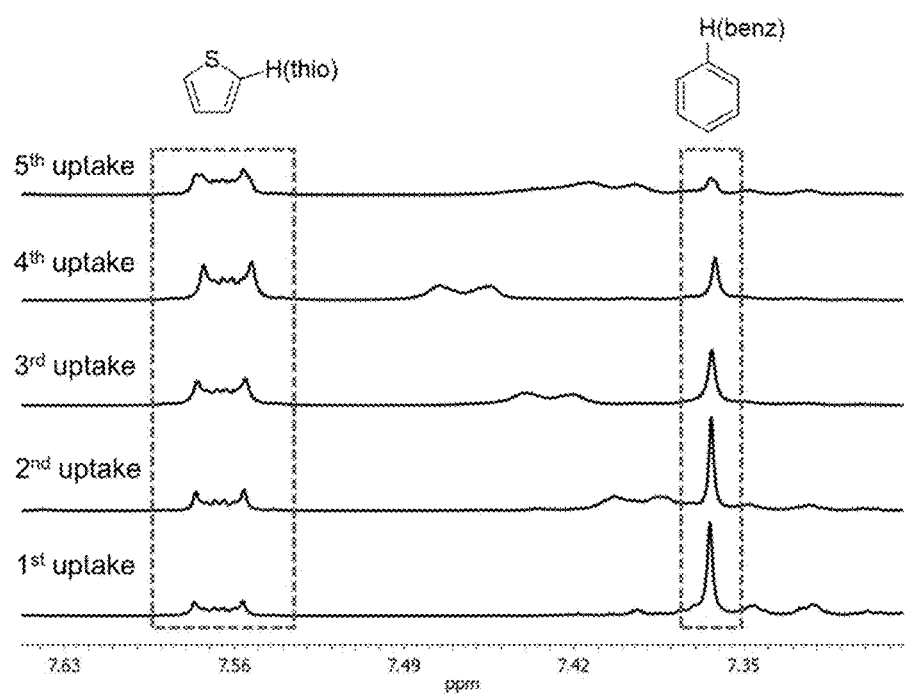
FIG. 8. $^1$H NMR spectra recorded during the thiophene uptake experiments (300 MHz, DMSO-d$_6$).
Figure 9:
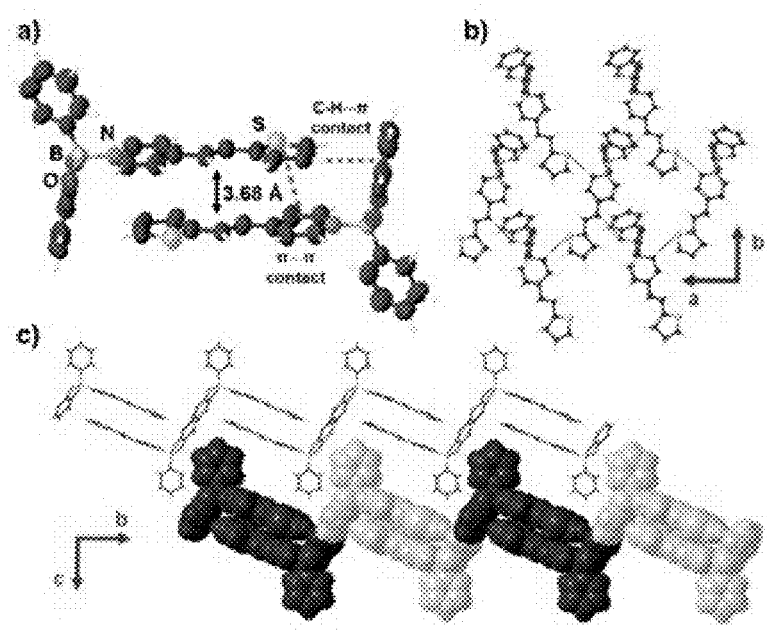
FIG. 9. X-ray structure (pbe)·(α-pte): (a) ORTEP view of face-to-face π-stacks, (b) extended view along ab-plane and (c) sheets parallel to b-axis.
Figure 10:
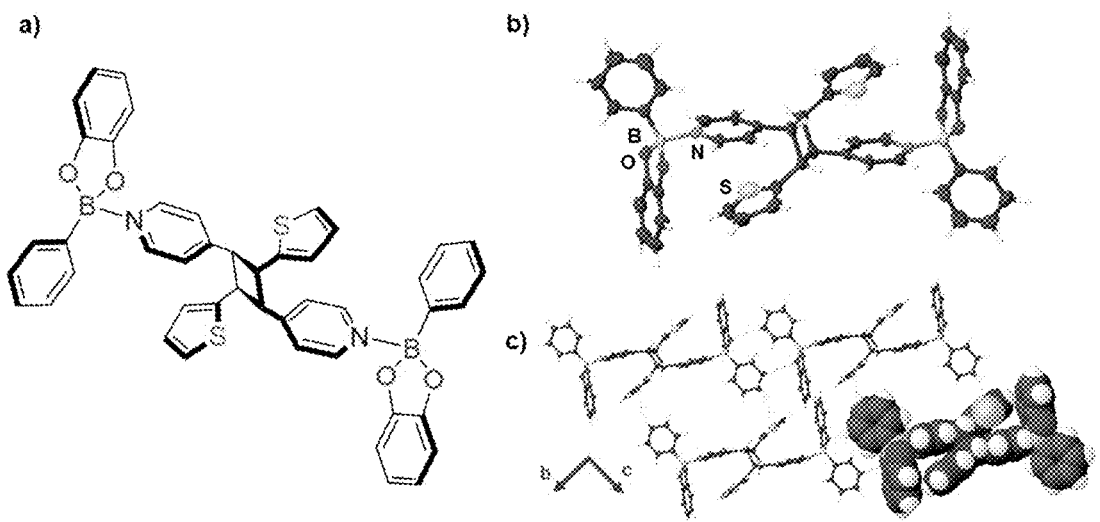
FIG. 10. (a) Molecular structure of 2(pbe)·(4p2tcb), (b) X-ray structure of 2(pbe)·(4p2tcb), and (c) extended view of 2(pbe)·(4p2tcb) packing in the solid state.
Figure 11:
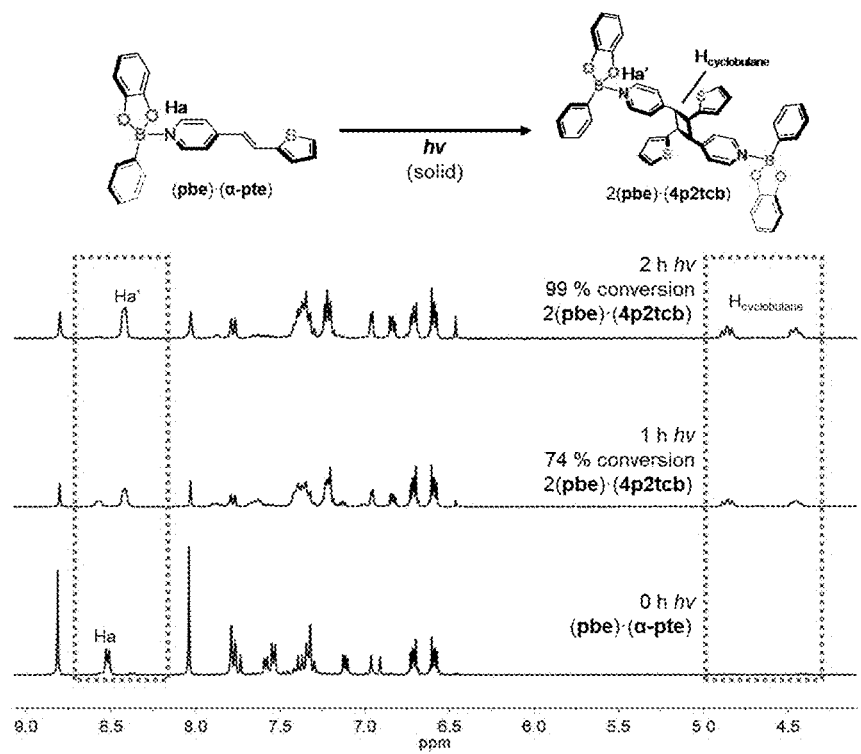
FIG. 11. $^1$H NMR spectra of photoreaction of (pbe)·(α-pte) at different time intervals with formation of 2(pbe)·(4p2tcb).
Figure 12:
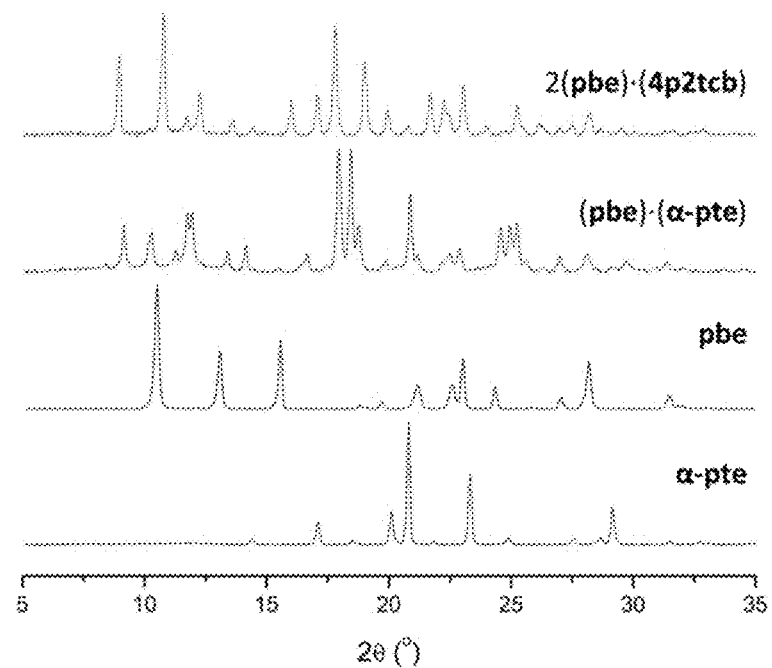
FIG. 12. Powder X-ray diffraction patterns of 2(pbe)·(4p2tcb) and starting materials.

This work shows that the bis-tweezer behavior of 2(1)·(ht-ppcb) can be exploited to separate thiophene from benzene (FIG. 5). The separation of thiophene from benzene is an important process in the petrochemical industry (Y. Zeng, et al., *J. Phys. Chem. C* 2015, 119, 15263-15273; H. Fu, et al., *J. Phys. Chem. C* 2017, 121, 25818-25826; and J. Weitkamp, et al., *J. Chem. Soc., Chem. Commun.* 1991, 1133-1134). The two aromatics not only have close boiling points, but can be exchanged isostructurally in the solid state (P. K. Thallapally, et al., *Tetrahedron* 2000, 56, 6721-6728). When powdered 2(1)·(ht-ppcb) was dissolved in a benzene/thiophene solution (1:1 ratio), a precipitate in the form of single crystals formed after a period of 2 d. Moreover, after five total cycles of repeated solvent uptake (G. Campillo-Alvarado, et al., *Cryst. Growth Des.* 2018, 18, 2726-2743), the thiophene:benzene composition was determined 94:6, as indicated by $^1$H NMR spectroscopy (FIG. 5a).

A single-crystal structure determination shows the components of 2(1)·(ht-ppcb)⊃6(C$_4$H$_4$S) to crystallize in the monoclinic space group C2/c. The asymmetric unit consists of three thiophene molecules that interact with the bis-tweezer (FIG. 5b). The thiophene molecules occupy nearly half of the crystal volume (46%), which contrasts the case of benzene for 2(1)·(ht-ppcb)⊃2(C$_6$H$_6$) (21%). The crystal lattice is also stabilized along the b-axis via C—H . . . O forces (FIG. 5b). Specifically, the thiophenes interact with the host by a combination of C—H . . . π (phenyl or pyridine), C—H(phenyl)S, and face-to-face π-π forces. The interactions involving the thiophene compare favorably to recent DFT calculations on interaction potentials of mixtures of benzene, thiophene, and pyridine as studied in the context of resin-asphaltene stability (O. Castellano, R. Gimon, H. Soscun, *Energy Fuels* 2011, 25, 2526-2541). The solid-state behaviour of the bis-tweezer 2(1)·(ht-ppcb) deviates from the benzene/thiophene exchange rule, which may tip the crystal landscape balance so as to enable the separation.

In summary, this work successfully demonstrates the use of a N→B bond to support reactivity in the solid state. A [2+2] photodimerization is achieved that generates a ditopic boronic ester adduct. The ditopic adduct forms through a rapid, regioselective, and quantitative cycloaddition to form a bis-tweezer host that includes benzene and thiophene. Separation of thiophene and benzene is realized using the diboron host. Current efforts are focused to study reactivity and optical properties conferred to solids by the N→B dative bond in supramolecular boron-based assemblies. That the N→B bond is employed to both direct the solid-state reaction and support a host material also motivates us to develop solids that exhibit more than one function (i.e. reactivity-→host behaviour) based on the same reversible linkage.

Certain embodiments of the invention will now be illustrated by the following non-limiting Examples.

EXAMPLES

Example 1

Synthesis of 2(1)·(ht-ppcb)⊃2(C$_6$H$_6$) and 2(1)·(ht-ppcb)⊃6(C$_4$H$_4$S)

Compound 2(1)·(ht-ppcb) is synthesized by placing 14.0 mg of powdered (1) (4-sbz) between a pair of Pyrex glass plates and irradiating it with UV-light (broadband UV-lamp, model PRIOR Lumen L200. Power supply: 240 v, 200 W.

Fuse rating F5A) for 20 minutes, flipping the sample after initial 10 min of exposure. The light source is placed 10 cm from the glass plates containing the sample. 2(1)·(ht-ppcb)⊃2(C$_6$H$_6$) is synthesized by dissolving 2(1)·(ht-ppcb) (13.0 mg) in a benzene/CHCl$_3$ mixture (4:1, 3.0 mL). The solution is sonicated and heated until it becomes clear and all the solid has dissolved. Slow evaporation of solvent affords single crystals as pale yellow plates after 3 days. 2(1)·(ht-ppcb)⊃6(C$_4$H$_4$S) was synthesized by dissolving 2(1)·(ht-ppcb) (14.0 mg) in thiophene (3.0 mL). The solution was sonicated and heated until it becomes clear and all the solid has dissolved. Slow evaporation of solvent affords single crystals as pale orange plates after 4 days.

(ht-ppcb). The signals H(thio) and H(benz) are normalized for the number of protons and performed a ratio analysis following the formula:

$$\frac{M(thio)}{M(benz)} = \frac{I(thio)}{I(benz)} \times \frac{N(benz)}{N(thio)}$$

Where I is the integral, and N is the number of nuclei giving rise to the signal. Since H(thio) consists of 2H (total of 4H) and H(benz) consists of 6H (total of 6H), the equation can be expressed as:

$$\frac{M(thio)}{M(benz)} = \frac{I(thio)}{I(benz)} \times \frac{6}{2}$$

TABLE 1

Crystallographic parameters for (1) · (4-sbz), 2(1) · (ht-ppcb)⊃2(C$_6$H$_6$) and 2(1) · (ht-ppcb)⊃6(C$_4$H$_4$S).

| Compound name | (1) · (4-sbz) | 2(1) · (ht-ppcb)⊃2(C$_6$H$_6$) | 2(1) · (ht-ppcb)⊃6(C$_4$H$_4$S) |
|---|---|---|---|
| Empirical formula | C$_{25}$H$_{20}$BNO$_2$ | C$_{31}$H$_{26}$BNO$_2$ | C$_{70}$H$_{60}$B$_2$N$_2$O$_4$S$_5$ |
| Formula weight | 377.23 | 455.34 | 1175.12 |
| Temperature/K | 298 | 298.15 | 190.15 |
| Crystal system | monoclinic | monoclinic | monoclinic |
| Space group | P2$_1$/n | P2$_1$/c | C2/c |
| a/Å | 10.3562(10) | 9.1565(9) | 23.379(2) |
| b/Å | 16.0851(16) | 25.025(2) | 9.4419(9) |
| c/Å | 12.7746(13) | 11.1787(11) | 27.732(3) |
| α/° | 90 | 90 | 90 |
| β/° | 105.226(5) | 95.034(5) | 97.004(5) |
| γ/° | 90 | 90 | 90 |
| Volume/Å$^3$ | 2053.3(4) | 2551.6(4) | 6075.9(10) |
| Z | 4 | 4 | 4 |
| ρ$_{calc}$g/cm$^3$ | 1.220 | 1.185 | 1.285 |
| μ/mm$^{-1}$ | 0.076 | 0.073 | 0.243 |
| F(000) | 792.0 | 960.0 | 2464.0 |
| Crystal size/mm$^3$ | 0.23 × 0.20 × 0.08 | 0.12 × 0.09 × 0.06 | 0.24 × 0.2 × 0.11 |
| Radiation | MoKα (λ = 0.71073) | MoKα (λ = 0.71073) | MoKα (λ = 0.71073) |
| 2θ range for data collection/° | 4.798 to 49.998 | 4.004 to 50.806 | 5.402 to 49.982 |
| Index ranges | −9 ≤ h ≤ 12, −17 ≤ k ≤ 19, −14 ≤ l ≤ 15 | −11 ≤ h ≤ 11, −30 ≤ k ≤ 30, −13 ≤ l ≤ 8 | −26 ≤ h ≤ 27, −11 ≤ k ≤ 9, −32 ≤ l ≤ 32 |
| Reflections collected | 10259 | 38684 | 61382 |
| Independent reflections | 3615 [R$_{int}$ = 0.0854, R$_{sigma}$ = 0.1095] | 4687 [R$_{int}$ = 0.0962, R$_{sigma}$ = 0.0769] | 5322 [R$_{int}$ = 0.0720, R$_{sigma}$ = 0.0422] |
| Data/restraints/parameters | 3615/0/262 | 4687/72/347 | 5322/1202/560 |
| Goodness-of-fit on F$^2$ | 1.004 | 1.008 | 1.005 |
| Final R indexes [I >= 2σ (I)] | R$_1$ = 0.0659, wR$_2$ = 0.1345 | R$_1$ = 0.0592, wR$_2$ = 0.1009 | R$_1$ = 0.0448, wR$_2$ = 0.0938 |
| Final R indexes [all data] | R$_1$ = 0.1979, wR$_2$ = 0.1766 | R$_1$ = 0.1748, wR$_2$ = 0.1373 | R$_1$ = 0.0843, wR$_2$ = 0.1145 |
| Largest diff. peak/hole/e Å$^{-3}$ | 0.18/−0.14 | 0.22/−0.13 | 0.19/−0.21 |
| CCDC deposition number | 1871328 | 1871329 | 1871330 |

Example 2

Thiophene Uptake

Slow evaporation of the starting materials of 2(1)·(ht-ppcb) in a 3 mL solution of a 1:1 benzene/thiophene mixture gave orange crystals after 2 days, which were collected and examined by $^1$H NMR spectroscopy. The $^1$H NMR spectrum analysis revealed that the crystals isolated contained 65% of thiophene. To analyze if the crystals could be enriched further with thiophene, the crystallization procedure was repeated starting from a mixture prepared with the ratio of benzene/thiophene as determined previously by $^1$H NMR spectroscopy. After the fifth consecutive uptake, the amount of thiophene in the crystals is increased to 94%.

The relative concentration analysis is carried out using the $^1$H NMR signals of H(thio) (2H of thiophene) and H(benz) (6H of benzene) in the δ 7.6-7.3 ppm region of the spectra taken from the single crystals after each uptake with 2(1)·

A summary of the results from Example 2 is provided in Table 2.

TABLE 2

| Thiophene uptake based on $^1$H NMR data | | | | |
|---|---|---|---|---|
| Uptake number | Relative M(thiophene) | Relative M(benzene) | Thiophene ratio (%) | Benzene ratio (%) |
| 1st | 6 | 3.28 | 65 | 35 |
| 2nd | 6 | 2.32 | 72 | 28 |
| 3rd | 6 | 1.32 | 82 | 18 |
| 4th | 6 | 0.78 | 90 | 10 |
| 5th | 6 | 0.40 | 94 | 6 |

Example 3

Synthesis of 2(pbe)·(4p2tcb)

Compound 2(pbe)·(4p2tcb) was synthesized by placing 50 mg of powdered (pbe) (α-pte) between a pair of Pyrex glass plates and irradiated it with UV-light (broadband UV-lamp, model PRIOR Lumen L200. Power supply: 240 v, 200 W. Fuse rating F5A) for 120 minutes, flipped the sample after initial 60 min of exposure. The light source was placed 10 cm from the glass plates containing the sample.

A summary of the results from Example 3 is provided in Table 3.

TABLE 3

Crystallographic parameters for (pbe) · (α-pte) and 2(pbe) · (4p2tcb)

| Compound name | (pbe) · (α-pte) | 2(pbe) · (4p2tcb) |
|---|---|---|
| Empirical formula | $C_{25}H_{18}BNO_2S$ | $C_{23}H_{18}BNO_2S$ |
| Formula weight | 382.68 | 383.25 |
| Temperature/K | 298.15 | 150.15 |
| Crystal system | monoclinic | monoclinic |
| Space group | $P2_1/n$ | $P2_1/n$ |
| a/Å | 10.4921(10) | 10.3635(9) |
| b/Å | 15.6355(16) | 14.989(3) |
| c/Å | 12.3827(12) | 12.741(2) |
| α/° | 90 | 90 |
| β/° | 97.966(5) | 90.8814(5) |
| γ/° | 90 | 90 |
| Volume/Å³ | 2011.8(3) | 1978.9(6) |
| Z | 4 | 4 |
| $\rho_{calc}$ g/cm³ | 1.263 | 1.286 |
| μ/mm⁻¹ | 0.176 | 0.182 |
| F(000) | 799.0 | 800.0 |
| Crystal size/mm³ | 0.23 × 0.2 × 0.1 | 0.2 × 0.2 × 0.1 |
| Radiation | MoKα (λ = 0.71073) | MoKα (λ = 0.71073) |
| 2θ range for data collection/° | 5.21 to 50 | 4.778 to 49.998 |
| Index ranges | −12 ≤ h ≤ 10, −18 ≤ k ≤ 18, −14 ≤ l ≤ 14 | −12 ≤ h ≤ 12, −17 ≤ k ≤ 17, −15 ≤ l ≤ 15 |
| Reflections collected | 9874 | 23487 |
| Independent reflections | 3502 [$R_{int}$ = 0.0643, $R_{sigma}$ = 0.0733] | 3489 [$R_{int}$ = 0.0503, $R_{sigma}$ = 0.0355] |
| Data/restraints/parameters | 3502/7/274 | 3489/0/254 |
| Goodness-of-fit on F² | 0.907 | 1.080 |
| Final R indexes [I >= 2σ (I)] | $R_1$ = 0.0537, $wR_2$ = 0.1293 | $R_1$ = 0.0886, $wR_2$ = 0.2004 |
| Final R indexes [all data] | $R_1$ = 0.1427, $wR_2$ = 0.1501 | $R_1$ = 0.1271, $wR_2$ = 0.2161 |
| Largest diff. peak/hole/e Å⁻³ | 0.10/−0.15 | 0.57/−0.40 |

Example 4

The Perfluorophenyl Analog

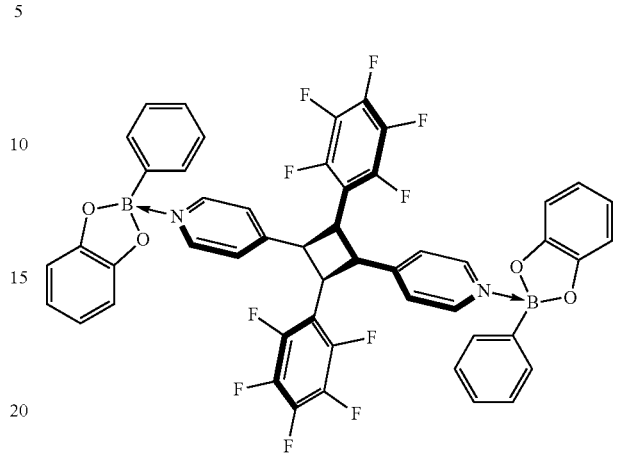

can be prepared as described by Campillo-Alvarado, G. et al. *Angew. Chem. Int. Ed.*, 2019, 58, 5413 and Campillo-Alvarado, G. et al. *Front. Chem.*, 2019, 7, 695.

All documents cited herein, including *Angew. Chem. Int. Ed.*, 2019, 58, 5413 and and Campillo-Alvarado, G. et al. *Front. Chem.*, 2019, 7, 695, are incorporated by reference. While certain embodiments of invention are described, and many details have been set forth for purposes of illustration, certain of the details can be varied without departing from the basic principles of the invention.

What is claimed is:

1. A compound of formula (I):

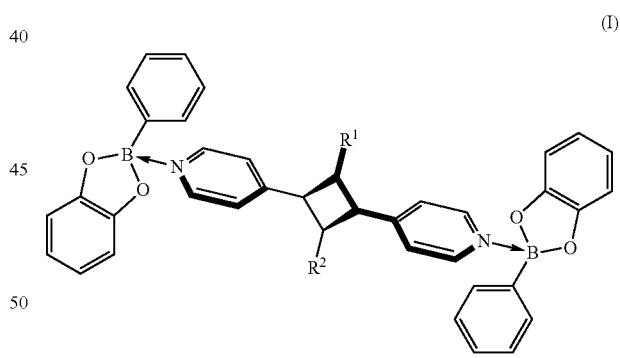

or a salt thereof, wherein:

$R^1$ is aryl or heteroaryl that is optionally substituted with one or more groups independently selected from the group consisting of nitro, carboxy, halo, cyano, ($C_1$-$C_6$)alkyl, ($C_3$-$C_6$)cycloalkyl, ($C_1$-$C_6$)alkoxy, ($C_2$-$C_6$)alkenyl, ($C_2$-$C_6$)alkynyl, ($C_1$-$C_6$)alkanoyl, ($C_1$-$C_6$)alkoxycarbonyl, ($C_1$-$C_6$)alkylthio, ($C_2$-$C_6$)alkanoyloxy, —OH and —C(=O)($C_1$-$C_6$ alkyl), wherein any ($C_1$-$C_6$)alkyl, ($C_3$-$C_6$)cycloalkyl, ($C_1$-$C_6$)alkoxy, ($C_2$-$C_6$)alkenyl, ($C_2$-$C_6$)alkynyl, ($C_1$-$C_6$)alkanoyl, ($C_1$-$C_6$)alkoxycarbonyl, ($C_1$-$C_6$)alkylthio and ($C_2$-$C_6$)alkanoyloxy is optionally substituted with one or more groups independently selected from the group consisting of halo, carboxy, —OH and cyano; and R² is aryl or heteroaryl that is optionally substituted with one or more groups independently selected from the group consisting of nitro, carboxy, halo, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, —OH and —C(=O)$(C_1-C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, —OH and cyano.

2. The compound or salt of claim 1, wherein R¹ is phenyl optionally substituted with one or more groups independently selected from the group consisting of nitro, halo, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, —OH and —C(=O)$(C_1-C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, —OH and cyano.

3. The compound or salt of claim 1, wherein R¹ is 2,3,4,5,6-fluorophenyl.

4. The compound or salt of claim 1, wherein R¹ is phenyl.

5. The compound or salt of claim 1, wherein R¹ is thiophenyl optionally substituted with one or more groups independently selected from the group consisting of nitro, halo, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, —OH and —C(=O)$(C_1-C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, —OH and cyano.

6. The compound or salt of claim 5, wherein R¹ is thiophenyl.

7. The compound or salt of claim 1, wherein R² is phenyl optionally substituted with one or more groups independently selected from the group consisting of nitro, halo, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, —OH and —C(=O)$(C_1-C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, —OH and cyano.

8. The compound or salt of claim 1, wherein R² is 2,3,4,5,6-fluorophenyl.

9. The compound or salt of claim 1, wherein R² is phenyl.

10. The compound or salt of claim 1, wherein R² is thiophenyl optionally substituted with one or more groups independently selected from the group consisting of nitro, halo, cyano, $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio, $(C_2-C_6)$alkanoyloxy, —OH and —C(=O)$(C_1-C_6$ alkyl), wherein any $(C_1-C_6)$alkyl, $(C_3-C_6)$cycloalkyl, $(C_1-C_6)$alkoxy, $(C_2-C_6)$alkenyl, $(C_2-C_6)$alkynyl, $(C_1-C_6)$alkanoyl, $(C_1-C_6)$alkoxycarbonyl, $(C_1-C_6)$alkylthio and $(C_2-C_6)$alkanoyloxy is optionally substituted with one or more groups independently selected from the group consisting of halo, carboxy, —OH and cyano.

11. The compound or salt of claim 10, wherein R² is thiophenyl.

12. A method for separating an aryl compound from a mixture comprising the aryl compound, said method comprising contacting the mixture with a ditopic boronic ester adduct, of claim 1 under conditions such that the aryl compound is separated from the mixture.

13. The method of claim 12 wherein the aryl compound is benzene, fluorobenzene, chlorobenzene, bromobenzene, iodobenzene, hydroxybenzene, aniline, furan, thiophene, 2-methylthiophene, 3-methylthiophene, 2,4-dimethylthiophene, benzothiophene, 2,3-dimethylbenzothiophene, 2,3,7-trimethylbenzothiophene, 2,3,4,7-tetramethylbenzothiophene, 2-methylbenzothiophene, dibenzothiophene, 4,6-dimethyldibenzothiophene, 2,4,6-dimethyldibenzothiophene, toluene, o-xylene, m-xylene, p-xylene, mesitylene, naphthalene, anthracene, phenanthrene, pyrene, coronene, tetrathiafulvalene, styrene or stilbene.

14. The method of claim 12, wherein the mixture comprising the aryl compound further comprises a non-aromatic organic solvent.

15. The method of claim 14 wherein the non-aromatic organic solvent is selected from the group consisting of halocarbons, ketones, esters, tetrahydrofuran, acetonitrile, dimethylformamide, and dialkyl ethers.

16. The method of claim 14 wherein the non-aromatic organic solvent is selected from the group consisting of chloroform, dichloromethane, carbon tetrachloride, acetone, ethyl acetate, tetrahydrofuran, acetonitrile, dimethylformamide, and diethylether.

17. The method of claim 12 wherein the ditopic boronic ester adduct is selected from the group consisting of:

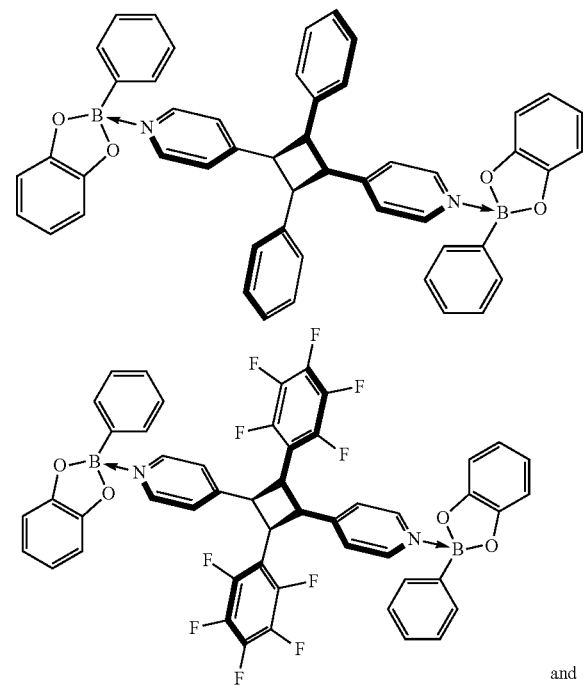

and

-continued

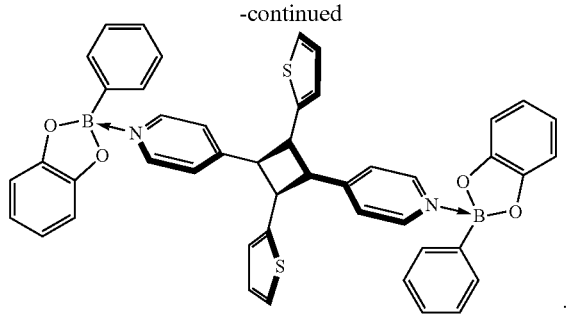

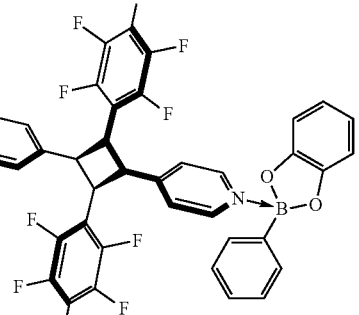

and

18. A method for purifying a hydrocarbon that comprises an impurity, comprising contacting a mixture comprising the hydrocarbon and the impurity with a ditopic boronic ester adduct of claim 1 under conditions such that the hydrocarbon is separated from the impurity.

19. The method of claim 18 wherein the impurity is benzene, thiophene, toluene, o-xylene or stilbene.

20. The method of claim 18 wherein the ditopic boronic ester adduct is selected from the group consisting of:

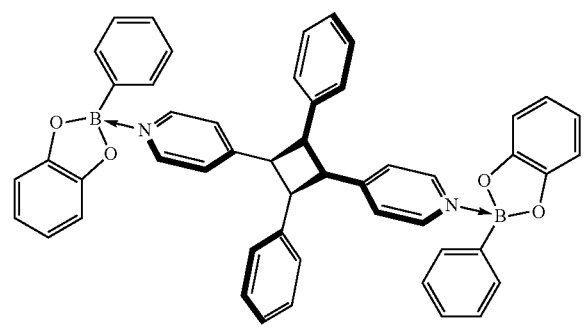

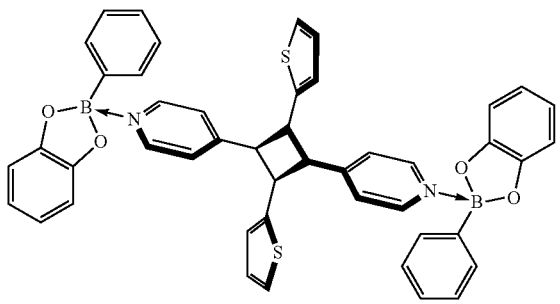

* * * * *